US007355376B2

(12) United States Patent
Gandhi et al.

(10) Patent No.: US 7,355,376 B2
(45) Date of Patent: Apr. 8, 2008

(54) BATTERY STATUS INDICATOR COMPENSATING FOR BATTERY VOLTAGE RECOVERY

(75) Inventors: Rajesh Gandhi, Woodbury, MN (US);
John Dyjach, Circle Pines, MN (US);
Shawn Kelley, Shoreview, MN (US);
Kristofer James, Eagan, MN (US);
Paul McNamee, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 385 days.

(21) Appl. No.: 11/072,905

(22) Filed: Mar. 3, 2005

(65) Prior Publication Data

US 2006/0197536 A1 Sep. 7, 2006

(51) Int. Cl.
*G05F 5/00* (2006.01)
*H02J 7/00* (2006.01)
*H01N 27/416* (2006.01)

(52) U.S. Cl. .............................. 323/299; 320/DIG. 11
(58) Field of Classification Search ................ 323/268, 323/273–276, 299, 303; 320/DIG. 11, DIG. 18, 320/DIG. 21; 324/426, 432, 433
See application file for complete search history.

(56) References Cited

U.S. PATENT DOCUMENTS

| 4,914,393 | A | * | 4/1990 | Yoshido | ...................... 324/428 |
| 4,952,864 | A | * | 8/1990 | Pless et al. | .................. 323/299 |
| 5,455,499 | A | * | 10/1995 | Uskali et al. | ............. 340/636.1 |
| 6,804,557 | B1 |   | 10/2004 | Kroll |   |
| 6,955,864 | B1 | * | 10/2005 | Vaisnys et al. | ............. 429/121 |
| 2003/0114897 | A1 |   | 6/2003 | Von Arx et al. |   |
| 2003/0114898 | A1 |   | 6/2003 | Von Arx et al. |   |
| 2003/0130708 | A1 |   | 7/2003 | Von Arx et al. |   |
| 2003/0148459 | A1 |   | 8/2003 | Von Arx et al. |   |
| 2004/0038424 | A1 |   | 2/2004 | Morrle et al. |   |

OTHER PUBLICATIONS

Guidant Corporation, Diagnostic Evaluation, pp. 6-5 to 6-18; Sep. 2003; www.guidant.com.
Guidant Corporation, Diagnostic Evaluation, pp. 6-5 to 6-18; Jul. 2004; www.guidant.com.
Guidant Corporation, Diagnostic Evaluation, pp. 6-6 to 6-18, Mar. 2004; www.guidant.com.

* cited by examiner

*Primary Examiner*—Matthew V. Nguyen
(74) *Attorney, Agent, or Firm*—Faegre & Benson LLP

(57) ABSTRACT

A method for determining a recovery voltage in a battery includes detecting a transient increased current draw event drawing current from the battery, the transient increased current draw event starting at a start time and ending at an end time; and in response to detecting the transient increased current draw event, waiting until time and/or voltage criteria are met to determine recovered battery voltage. An implantable pulse generator (PG) device for stimulating a human organ includes a battery, a power sink drawing current from the battery, wherein drawing increased current from the battery for transient periods causes battery voltage to decrease; and a status indicator detecting a transient increased current draw event and waiting a minimum time duration after the transient increased current draw event to measure battery voltage in order to determine a recovery voltage.

23 Claims, 9 Drawing Sheets

BATTERY STATUS INDICATOR COMPENSATING FOR BATTERY VOLTAGE RECOVERY

BACKGROUND

Batteries have limited life spans. When the charge is depleted in a battery, the battery-powered device will cease to function. To circumvent loss of functionality, the battery must be replaced or recharged prior to charge depletion. Accurate determination of a battery's state of depletion is particularly important for battery-powered medical devices that are implanted in human patients. With an accurate determination of battery depletion state, an implanted medical device may be recharged or replaced in order to maintain therapy.

Pulse generators (PGs) are battery-powered medical devices that are implanted in patients and provide electrical pulses (therapy) to stimulate or shock the patient's heart. PGs include cardiac rhythm management (CRM) devices, such as pacemakers, heart failure devices, and defibrillators. Batteries serve as the power source in the PGs, providing power to, for example, generate the pulses, sound a beeper when necessary, and upload recorded data via telemetry. Replacement of the PG when the battery is depleted requires surgery. The consequences of not replacing the PG prior to the point at which battery charge is depleted, however, could deprive the patient of therapy and therefore be life-threatening. Accurate determination of a PG battery's charge supports an effective assessment of the appropriate replacement time, not only allowing the clinician to ensure therapy is available, but also allowing the clinician to maximize time until replacing the PG (i.e., maximize time between surgeries).

Battery voltage is often used as an indicator of remaining battery charge. If voltage is above a threshold, the charge remaining is considered sufficient. Unfortunately, many batteries exhibit aberrant voltage behavior during and following transient periods of increased current draw (e.g., when the beeper is sounding in a PG, when PG telemetry is active, or when a PG charges before delivering a defibrillation shock to the heart). The aberrant voltage behavior is not indicative of the charge in the battery. As such, reliance upon such aberrant voltages can be misleading for purposes of determining battery charge.

To illustrate, FIG. 1 graphically depicts a battery voltage response 102 during a period of high current draw. Voltage is shown with a solid line 102 and current is shown with a dotted line 104. Prior to time $t_{start}$, voltage is at an initial, steady-state average level 106, and current is at a relatively low steady-state average level (e.g., 10 μA-100 μA). At $t_{start}$, current increases to a high current level 108. In response to the increase in current draw, voltage 102 begins to decrease. During the current draw event, voltage decreases to a low voltage level 110. Current 104 remains at the high level 108 until time $t_{end}$. At time $t_{end}$, current 104 returns to a low level, and voltage 102 begins to increase. The time period between $t_{start}$ and $t_{end}$ is referred to herein as a transient period of increased current draw, or a transient period of decreased voltage.

The period after $t_{end}$ when voltage is returning to a steady-state average value is referred to as the recovery period. Typically, during the recovery period, the voltage increases to a recovery voltage, $V_R$, 112. The recovery voltage $V_R$ 112 may or may not be equal to the initial voltage level 106. Illustrated in FIG. 1 are two typical voltage recovery scenarios. A first scenario, depicted with solid line 114, involves voltage overshoot. In the overshoot scenario 114, the voltage 102 increases higher than recovery voltage, $V_R$, 112 and then converges on $V_R$, 112. In the overshoot scenario 114, the voltage may fluctuate around $V_R$ 112 before converging. A second voltage recovery scenario, depicted with dotted-dashed line 116, does not involve voltage overshoot. In the second scenario, the voltage 102 continues to increase up to $V_R$ 112.

The transient decreased voltage (i.e., the voltage between time $t_{start}$ and $t_{end}$) is not considered a valid voltage for purposes of determining the charge remaining, because the voltage is not representative of the steady-state voltage in the battery. In addition, the recovery period for different transient current draw events is variable; it can last minutes, hours, or even days. The length of the recovery period typically depends on the magnitude and duration of the transient increased current draw event, the type of battery, depletion of the battery and other conditions. As a result, an indication of battery charge based on the voltage measured during the transient period and/or during the recovery period may not accurately reflect the true charge held by the battery.

Some products in the past have precluded use of battery voltage measurements made within a fixed 24-hour period of high-voltage charge events. As voltage response to increased current draw can vary considerably with battery type, use of a fixed 24-hour period has the potential to be too short for batteries that exhibit a slow voltage recovery, or needlessly long for batteries that exhibit a long voltage recovery. Using a fixed 24-hour period has the potential to be too short for large magnitude events and needlessly long for small magnitude events. Using a voltage that is still recovering from a large magnitude event or slow recovering batteries may report a voltage that is too low. A low voltage would be interpreted as battery depletion that is greater than actual. Use of a needlessly long period for a small magnitude event or fast recovering batteries could deprive the system of voltage measurements and prevent reporting charge state of the battery. As such, a fixed 24-hour period following only high-voltage charge events does not take into account the either the range of battery types or the range of events that may be encountered.

Thus, a need exists for a method and system for accurately detecting and/or indicating battery charge status despite aberrant voltage response due to a range of transient increased current draw events.

SUMMARY

Embodiments of systems and methods described provide for accurately detecting and indicating recovery voltage for use in determining battery charge status. Described embodiments use voltage-related criteria and/or time-related criteria to dynamically determine recovery voltage after transient increased current draw events. According to various embodiments, the determined recovery voltage may be an actual measured voltage or an estimated or predicted voltage.

An embodiment of a method includes detecting a transient increased current draw event starting at a start time and ending at an end time, selecting a battery voltage measurement that is measured after the end time based on time-related or voltage-related criteria; and determining the recovery voltage using the selected battery voltage measurement, wherein the recovery voltage represents a voltage level to which battery voltage is expected to recover after the transient increased current draw event.

Embodiments of computer-readable media include processor-executable instructions, which, when executed by a processor, cause the processor to perform a process for determining a recovery voltage associated with a battery. One embodiment of the process includes detecting a transient increased current draw event that draws current from the battery starting at a start time and ending at an end time, obtaining a first battery voltage measurement after the end time and a subsequent battery voltage measurement after the end time, and determining the recovery voltage by determining whether the difference between the first battery voltage measurement and the subsequent measured battery voltage measurement is less than a specified voltage change.

An implantable pulse generator (PG) device for stimulating a human organ includes a battery, a power sink drawing current from the battery when activated, wherein drawing current from the battery causes battery voltage to decrease; and a status indicator detecting a transient increased current draw event and, utilizing preceding battery voltage measurement(s), subsequent battery voltage measurement(s), or details about the event to determine a valid post-event recovery voltage that is indicative of battery status.

A more complete understanding of the present invention may be derived by referring to the detailed description of preferred embodiments and claims when considered in connection with the figures.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION

Embodiments described herein relate generally to determining battery recovery voltage by compensating for aberrant voltage behavior due to a transient increased current draw event. When a transient increased current draw event is detected, various operations are performed to avoid reliance on aberrant voltages in order to obtain a valid recovery voltage that can be used to more accurately determine the charge remaining in the battery.

In various embodiments, battery voltage measurements obtained during the transient increased current draw event are not used in determining recovery voltage. According to various embodiments, one or more voltage measurements are obtained after the transient increased current draw event and used to determine actual recovery voltage and/or estimated recovery voltage. In addition, rate of change in voltage during the recovery period can be used to determine recovery voltage. The magnitude of variation from a voltage obtained prior to the event may also be used to determine recovery voltage.

The term "time-related criteria" refers to one or more rules or tests that are applied to determine a result based on time. Because the time-related criteria are based on time, the result may vary as time varies. Similarly, "voltage-related criteria" refers to one or more rules or tests that are applied to determine a result based on voltage. Results obtained using voltage-related criteria may vary as voltage varies. By using time-related criteria and voltage-related criteria to determine recovery voltage in various embodiments, the determined recovery voltage is based on a dynamic understanding of a current state of the battery-powered device.

Figure 2:
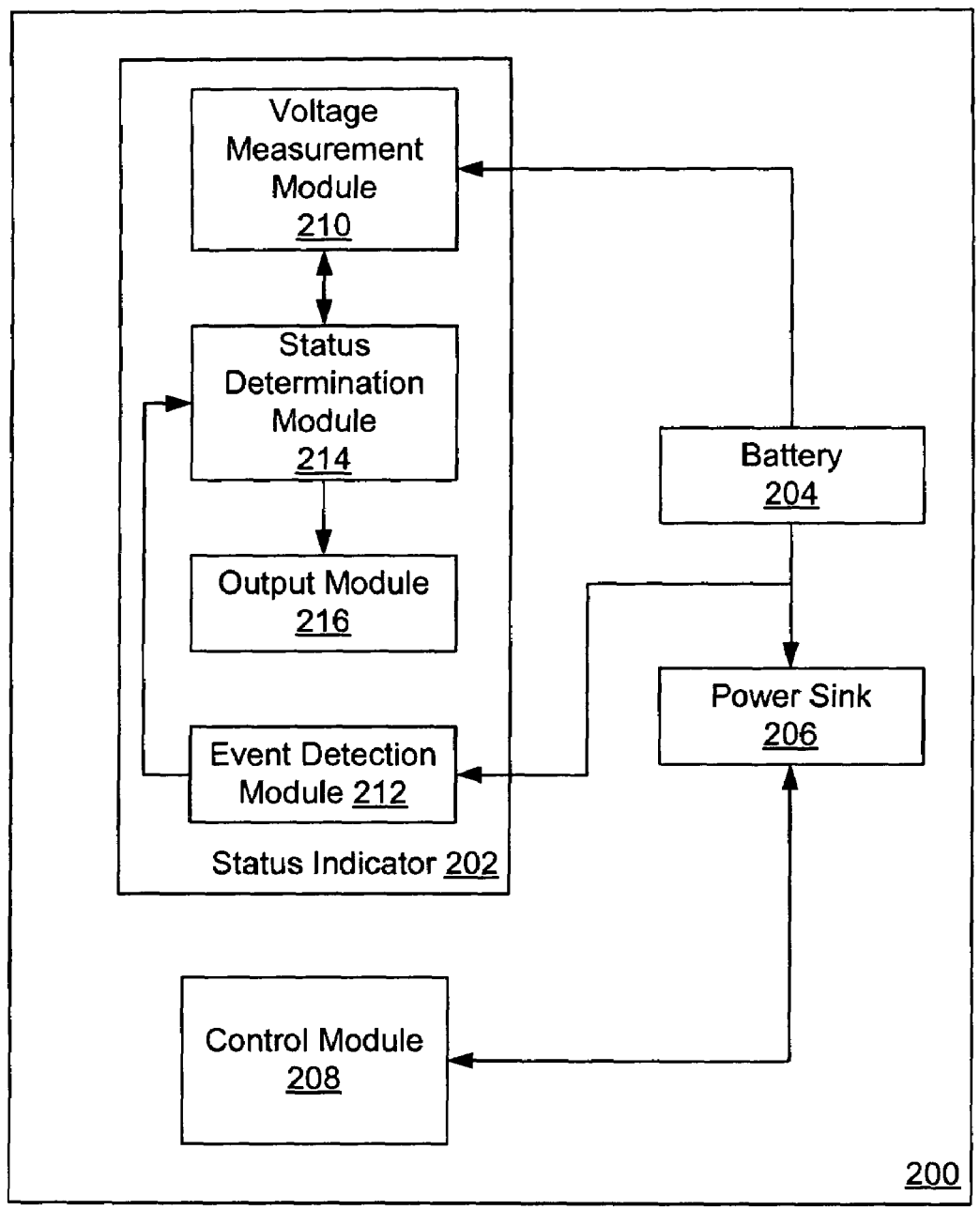
FIG. 2 illustrates an exemplary device employing battery power, wherein a battery status indicator determines and indicates the status of battery voltage.

FIG. 2 illustrates one embodiment of an exemplary battery-powered device 200 in which a battery status indicator 202 determines and indicates the status of voltage available in a battery 204. The device 200 is representative of any number of implantable battery-powered devices. By way of example, but not limitation, the device 200 can represent an implantable pulse generator (PG) device, such as a cardiac pacemaker, an implantable cardioverter defibrillator, a neurostimulator, or a cardiac resynchronization therapy device. In such devices, pulses are generated to stimulate an organ (e.g., heart) in a patient. Typically, in an implantable PG device, current is drawn from the battery 204. Power-consuming components, such as a beeper, telemetry circuitry, therapy circuitry, and/or any other power consuming circuitry in the PG device, are referred to generally as power sinks.

For illustration, a particular embodiment of the battery-powered device 200 is an implantable cardioverter defibrillator. A cardioverter defibrillator delivers electrical shocks to the heart to eliminate abnormal rhythms such as ventricular fibrillation or ventricular tachycardia. Typically, the cardioverter defibrillator monitors heart function for an arrhythmia. When a shock is needed, the capacitor is charged. Upon completion of charging, the capacitor energy is discharged into the heart. Charging the capacitor requires a transient increased current draw from the battery.

Although particular embodiments described herein relate to implantable PG devices, it is to be understood that the battery-powered device 200 is not limited to implantable PG devices. For example, in another embodiment, the battery-powered device 200 could be a sensor that is implanted in the human body. Such a sensor would gather data and use telemetry to communicate the data. The telemetry circuitry of the sensor and sensor itself may be considered a power sink.

Accordingly, in a general sense, the battery 204 supplies power (e.g., direct current) to a power sink 206. The battery 204 has an associated chemistry. In one embodiment, the battery 204 has a Lithium Manganese Dioxide (Li/MnO$_2$) chemistry. In other embodiments, other chemistries may be used, such as, but not limited to, Li/Ag$_x$V$_y$O$_z$ or Li/CF$_x$, or Li/SOCl$_2$ or other non-lithium battery chemistries. These, and other types of battery chemistries exhibit aberrant voltage behavior in response to a transient increased current draw event; however, the voltage behavior is unique for each chemistry.

Figure 1:
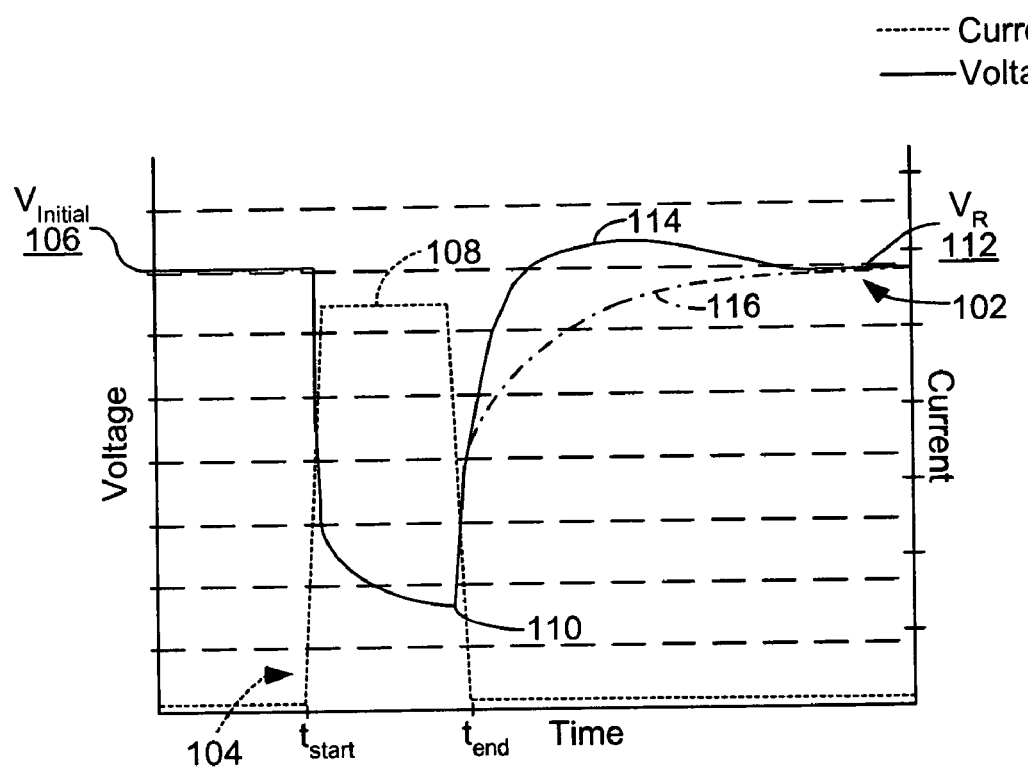
FIG. 1 illustrates voltage response in a battery due to current being drawn from the battery.

As used herein, a power sink 206 is any functional component requiring battery power to operate. A control module 208 controls the operation of the power sink 206 by sending signals to the power sink 206. Under steady-state conditions, the power sink 206 draws current from the battery 204 at a steady-state, relatively low level. However, sometimes the control module 208 activates a high current function (e.g., beeper, telemetry, etc.) in the power sink 206, which results in an increased current draw event. Typically, the function is only required for a finite time period. At some time after activating the function, the control module 208 signals the power sink 206 to stop the function, and the current draw returns to the steady state low level. As discussed above with respect to FIG. 1, when current is drawn at an increased level, the voltage response can be aberrant or invalid for purposes of determining battery status for some time.

As such, the status indicator 202 employs various modules for accurately determining and indicating the status of voltage available from the battery 204, despite the aberrant voltage response. In the exemplary embodiment shown in FIG. 2, the status indicator 202 includes a voltage measurement module 210, an event detection module 212, a status determination module 214, and an output module 216. In one embodiment, the modules in the status indicator 202 communicate with each other to carry out operations involved in determining and indicating battery 204 status.

The term module is used in a general sense to describe a component that is operable to perform one or more designated functions. A module can be implemented in various ways and forms. For example, a module may be implemented in any combination of hardware, software, or firmware. By way of example, but not limitation, the modules shown in FIG. 2 may be implemented with a microprocessor executing instructions stored in memory. As another example, one or more of the modules may be implemented in an application specific integrated circuit (ASIC). As yet another example, one or more of the modules may be implemented using discrete components. As still another example, one or more of the modules in FIG. 2 may be implemented with a field programmable gate array (FPGA).

Referring again to the status indicator 202, the status determination module 214 uses data from the event detection module 212 to determine when and how to analyze voltage measurements from the voltage measurement module 210. The event detection module 212 determines when a transient increased current draw event occurs. As used herein, a transient increased draw event is an event in which current being drawn from the battery 204 is at a higher than steady-state level.

The event detection module 212 sends signals to the status determination module 214 to notify the status determination module 214 when a transient increased current draw event is imminent, is occurring, or has ended. One embodiment of the event detection module 212 includes a current measurement circuit that detects an increase in current from the battery 204. In this embodiment, the current measurement circuit monitors current flowing between the power sink 206 and the battery 204. When the current rises above the predefined threshold, a signal is output from the current measurement circuit indicating the transient increased current draw. When the current drops below the predefined threshold, the current measurement circuit outputs another signal indicating the end of transient increased current draw event. In other embodiments, the event detection module identifies activities the PG is performing that result in increased current draw.

Based on the signals from the event detection module 212, the status determination module 214 obtains voltage measurements from the voltage measurement module 210 to analyze voltage status in the battery 204. The voltage measurement module 210 measures voltage across terminals of the battery 204 and transmits the measured voltage to the status determination module 214. The status determination module 212 can analyze one or more selected measured voltage(s) at selected time(s) to determine whether battery 204 voltage is recovered.

The status determination module 214 can apply one or more types of voltage analyses to determine if the voltage is valid. In one embodiment, the status determination module 214 controls the voltage measurement module 210 to take measurements at specified time(s), depending on the type of validity analysis being performed. FIGS. 3b, 4b, 4c, and 5b illustrate algorithms associated with various exemplary analyses that can be performed to determine the validity of the voltage. The status determination module 214 is configurable to carry out one or more of the algorithms shown in FIGS. 3b, 4b, 4c, and 5b. FIGS. 3-5 are discussed in detail below.

Based on the voltage analysis, the status determination module 214 sends status data to the output module 216. The status data can be more or less complex, depending on the particular application. For example, in one embodiment, the status data is simply "Valid" or "Invalid" to indicate that the voltage is valid or invalid, respectively, for purposes of determining charge in the battery 204. In another embodiment, a voltage value and/or battery charge value is sent to the output module 216 along with an associated time of measurement and an indication of the validity.

The output module 216 makes the status data available for output. By way of example, the output module 216 may store the status data in a memory for later retrieval. As another example, the output module 216 may automatically upload the data to a receiving device (e.g., a PG programmer or other computing and/or display device) using telemetry or another data transmission mechanism. As yet another example, the output module 216 may cause the status data to be displayed on a display device, such as a PG programmer or other external display device.

The charge remaining in the battery 204 may be calculated by a remote computing device that uploads the voltage data from the status indicator 202, or the charge remaining may be calculated by the status indicator 202 itself. For example, one embodiment of the status determination module 214 determines battery charge status based on the determined valid voltage. The remaining charge in the battery is related to the voltage as expressed in Equation (1), below:

$$\text{Charge Remaining} = f(V_R), \quad \text{Eq. (1):}$$

wherein $V_R$ represents the recovery voltage. As shown below, using some algorithms, $V_R$ is estimated or predicted, while using other algorithms, $V_R$ is a measured voltage. In this embodiment, the status determination module 214 can send the remaining charge and/or the voltage to the output module 216.

In another embodiment of the device 200, the status indicator 202 is implemented as part of the control module 208. In this embodiment, one or more of the modules in the status indicator may not need to be separate modules. For example, because the control module 208 determines when a current draw event occurs, in this embodiment the event detection module 210 may not be necessary as a separate module.

Although each of the modules shown in FIG. 2 is depicted as performing its own function, it is to be understood that the modules are not limited to their functions described in FIG.

2. One or more of the modules shown in FIG. 2 could be combined into a single module, or the functions of one module could be carried out by one or more of the other modules.

Referring more specifically to operations that are performed by the status indicator 202, in one embodiment, voltage measurements during a transient increased current draw event are not used to determine recovery voltage. In this embodiment, voltage measurement can be postponed until after the transient increased current draw event, or measurements can be taken but not used in to determine recovery voltage. To illustrate, reference is made to FIG. 1. In this embodiment, the status determination module 214 does not use any voltage measurements during the transient period (i.e., between $t_{start}$ and $t_{end}$) in determining recovery voltage.

In some embodiments, the status indicator 202 waits a determined time duration after $t_{end}$ before measuring battery voltage for purposes of determining the recovery voltage. In these embodiments, the time duration to wait may be based on various conditions, such as battery chemistry or type of transient increased current draw event. FIG. 3 depicts an exemplary embodiment that determines time duration based on such conditions.

In other embodiments, the time duration to wait may be independent of battery chemistry and the type of transient increased current draw event. In these embodiments, the time duration may be determined based on voltage-related criteria or time-related criteria. FIG. 4 depicts an exemplary embodiment using voltage-related criteria and/or time-related criteria.

The event detection module 212 notifies the status determination module 214 when the transient increased current draw event starts at time $t_{start}$. In one particular embodiment, the status determination module 214 commands the voltage measurement module 210 to stop measuring voltage. Later at time $t_{end}$, the event detection module 212 notifies the status determination module 214 that the transient increased current draw event has ended. The status determination module 214 waits a specified time duration and then commands the voltage measurement module 210 to measure the voltage. The measured voltage is used to determine battery status. The time duration can be set to any value depending on the particular application, with typical values ranging from 10 ms to multiple hours. By waiting until after $t_{end}$ to use voltage measurements, the status determination module 214 uses voltage measurements that are made during steady state current draw conditions to determine recovery voltage, which represents battery voltage that has recovered or will recover from a decrease in voltage due to the transient period of increased current draw.

Figure 3A:
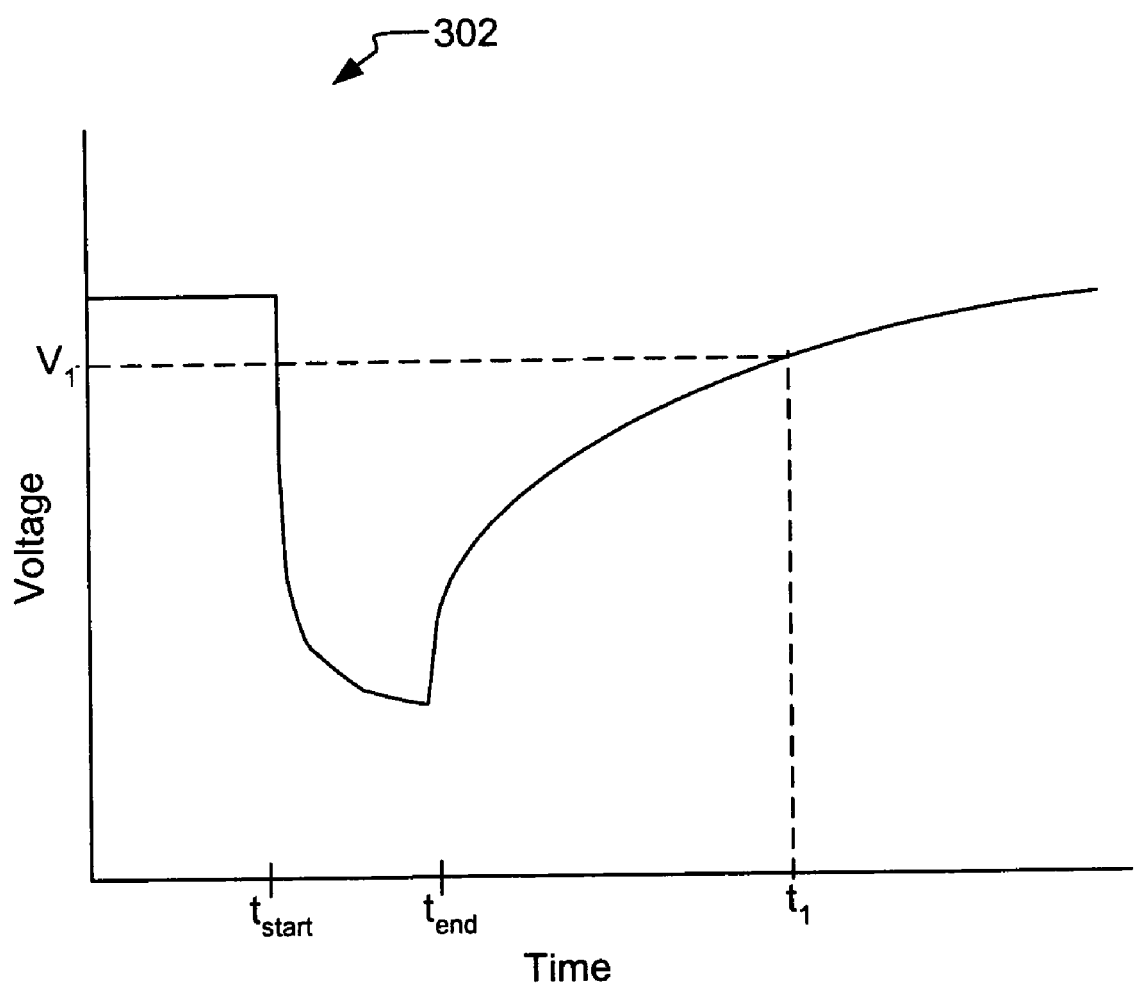
FIGS. 3A-3B illustrate an exemplary algorithm for determining recovery voltage by measuring voltage at a time that is selected based on various conditions or settings.
Figure 3B:
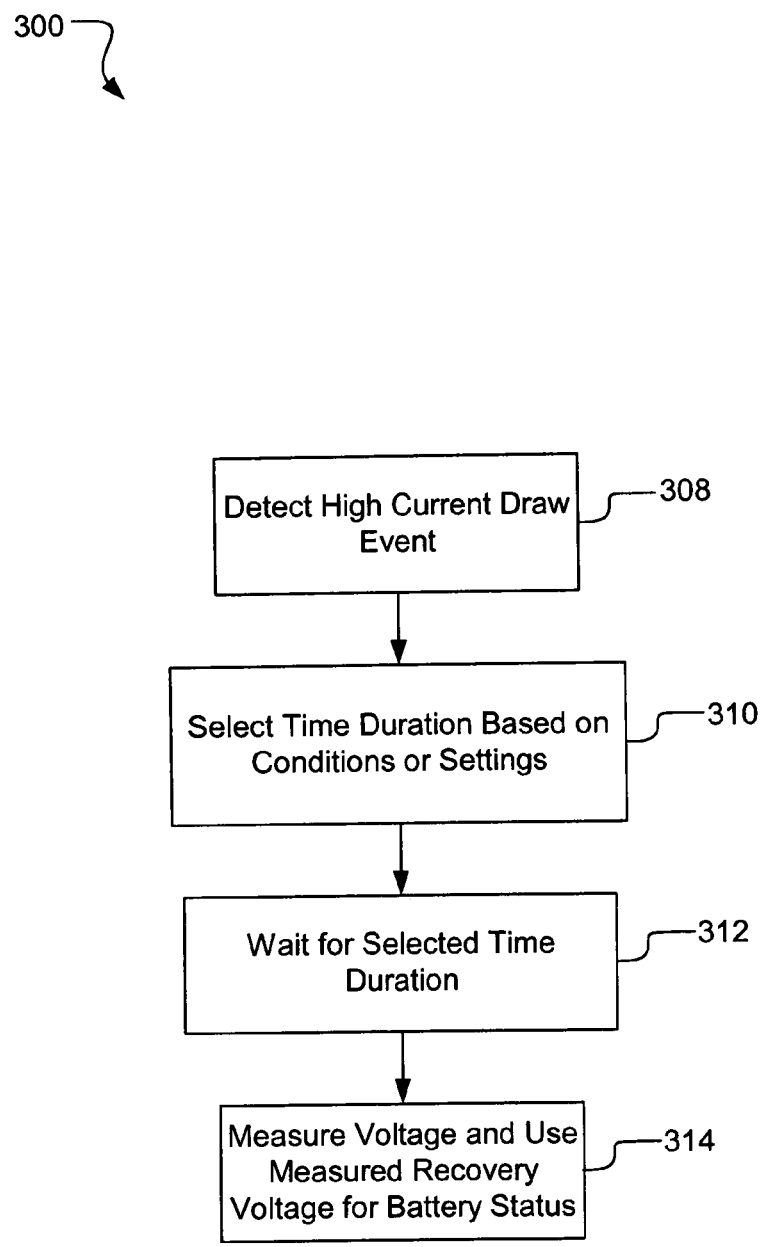

FIGS. 3A and 3B illustrate an exemplary recovery voltage determination algorithm 300 for determining battery status. Referring to FIG. 3A, a voltage response 302 is depicted, wherein a transient increased current draw event starts at time $t_{start}$ and ends at time $t_{end}$. Generally, battery voltage, $V_1$, is measured at time $t_1$ relative to the current draw event, wherein the time $t_1$ is determined based on one or more conditions or settings. Thus, in this embodiment, the time when the voltage is measured after the transient increased current draw event may vary from one transient increased current draw event to another transient increased current draw event. In this embodiment, $t_{end}$ is used to determine a measurement time, $t_1$.

In this embodiment, the time, $t_1$, to measure battery voltage, $V_1$, is expressed with Equation (2):

$$t_1 = t_{end} + T_{min}, \quad \text{Eq. (2)}$$

wherein $T_{min}$ represents a time duration to wait after $t_0$ to measure voltage. In one embodiment, $T_{min}$ is a design parameter. It other embodiments, $t_{start}$, or some other time between $t_{start}$ and $t_{end}$ could be used in Eq. (2). This embodiment can be used when voltage overshoot is present by selecting $t_1$ such that the absolute value of $(V_{Recovered} - V_1)$ is less than a specified maximum voltage delta.

With more specific regard to FIG. 3B, the recovery voltage determination algorithm 300 includes exemplary operations that can be carried out by the device 200 of FIG. 2 or any other suitable device. Initially, a detecting operation 308 detects the start of the transient increased current draw event. The transient increased current draw event can be detected in a number of ways. By way of example, and not limitation, the transient increased current draw event can be detected based on an activation signal to the power sink component, a measurement of current from the battery (e.g., via a current measurement circuit), or data within the device that indicates activation of a transient increased current draw event.

As discussed above, when the transient increased current draw event begins, the battery voltage typically drops. The extent of the voltage drop depends on a number of factors including, but not limited to, the magnitude of the transient increased current event, the type of transient increased current event, the type of battery chemistry, charge depletion, temperature, or the general level of activity of the device.

A selecting operation 310 selects time duration, $T_{min}$, based on one or more conditions or settings. In one embodiment, the selecting operation 310 selects the time duration based on the type of transient increased current draw event that has occurred or is occurring. In this embodiment, a different time duration can be stored (e.g., at manufacture time) in memory for each type of transient increased current draw event. Thus, for example, a PG may have a time duration stored for each of a number of transient increased current events such as, the beeper, telemetry communication, or a high-energy charge event. In this embodiment, during operation the selecting operation 310 determines the type of transient increased current event and selects the corresponding $T_{min}$ value from memory.

Another embodiment of the selecting operation 310 selects the time duration based on the magnitude of the transient increased current draw event. In this embodiment, the magnitude of the transient increased current draw event is assessed. This may involve, for example, determining the level of voltage drop due to the transient increased current draw, the charge consumed during the transient increased current draw event, or determining the duration of the transient increased current draw event. Because the voltage may be affected differently based on battery type, the type of battery may also be taken into account.

It will be understood by those skilled in the art that there may be numerous ways to determine the time duration, in addition to those set forth here. The selecting operation 310 may be embodied as a computation (e.g., based on the specific magnitude/duration of the transient increased current event), lookup values, or fixed values. Associated fixed values, lookup values, or computation parameters may be stored as field programmable or factory programmable values in memory. During the selecting operation 310, the programmed parameters are read from memory and used to delay voltage measurement.

A waiting operation 312 waits the selected time duration. During the waiting operation 312, the voltage may or may not be measured. Any measurements that are made during the waiting operation 312 are not used to determine the status of voltage in the battery. Measuring operation 314 measures the battery voltage after waiting the selected time duration, $T_{min}$. The voltage measured in measuring operation 314 after the selected time duration is assumed to be a valid recovery voltage. As such, the voltage measured in the measuring operation 314 is used to determine battery status.

Figure 4A:
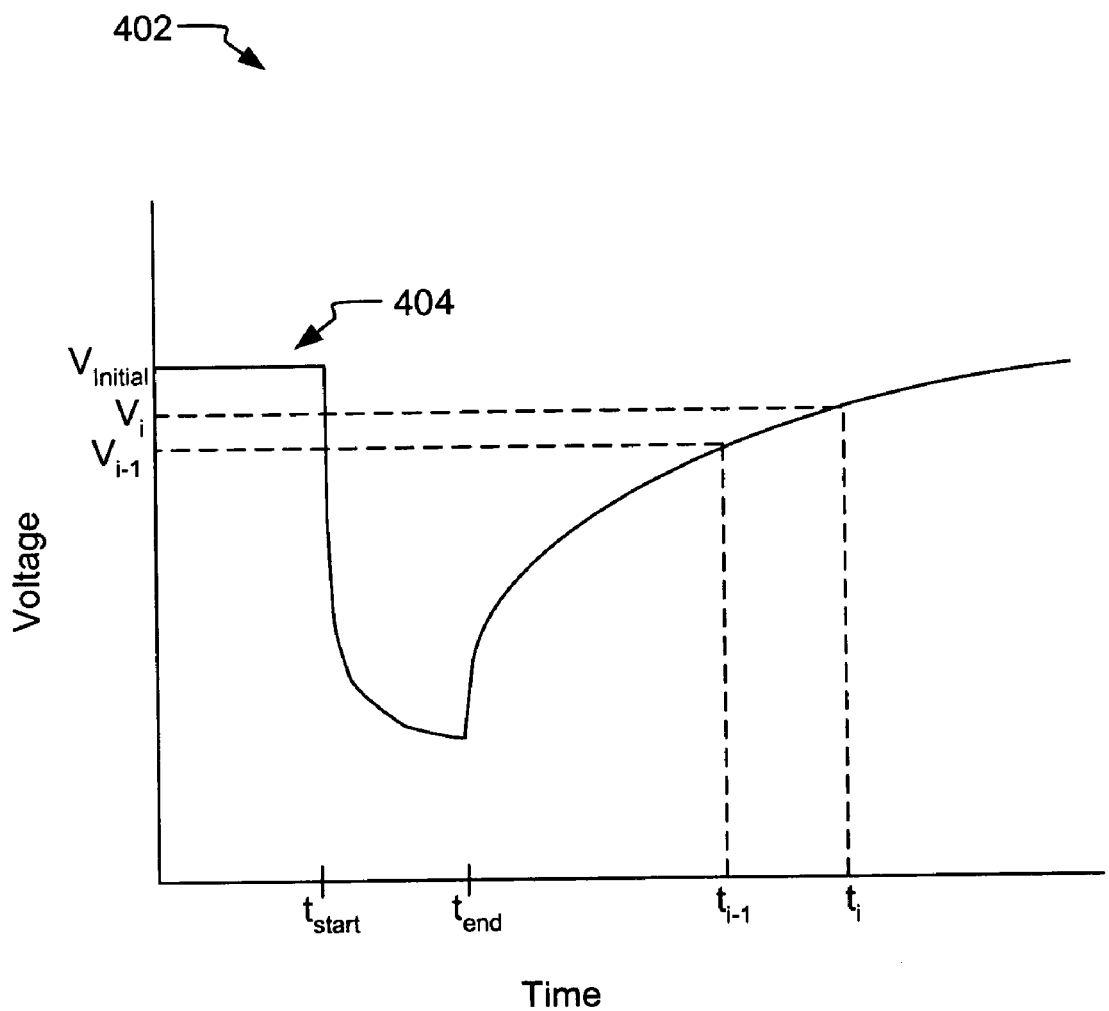
FIGS. 4A-4C illustrate other exemplary algorithms for determining recovery voltage based on changes in battery voltage over time during the recovery period.
Figure 4B:
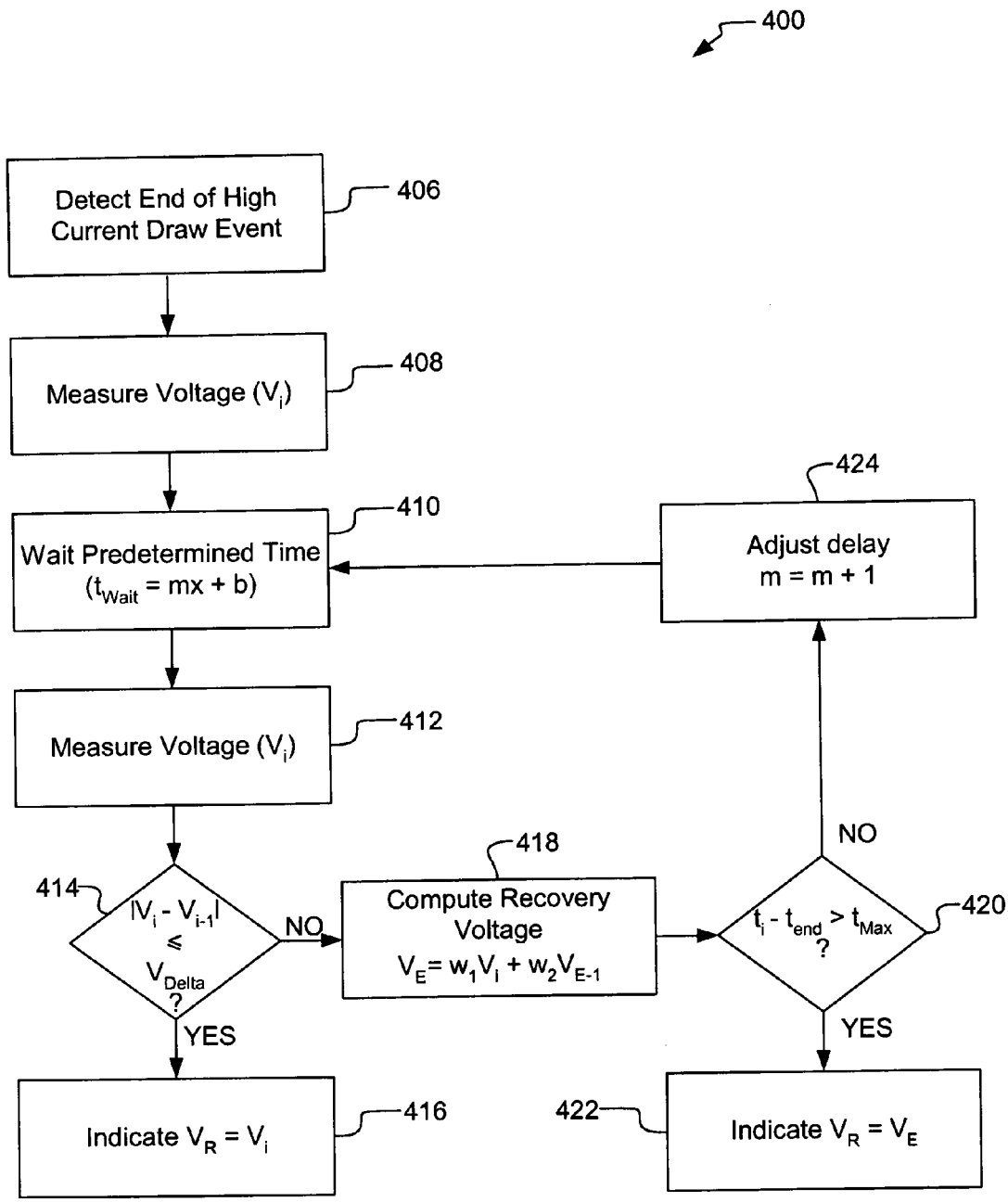
Figure 4C:
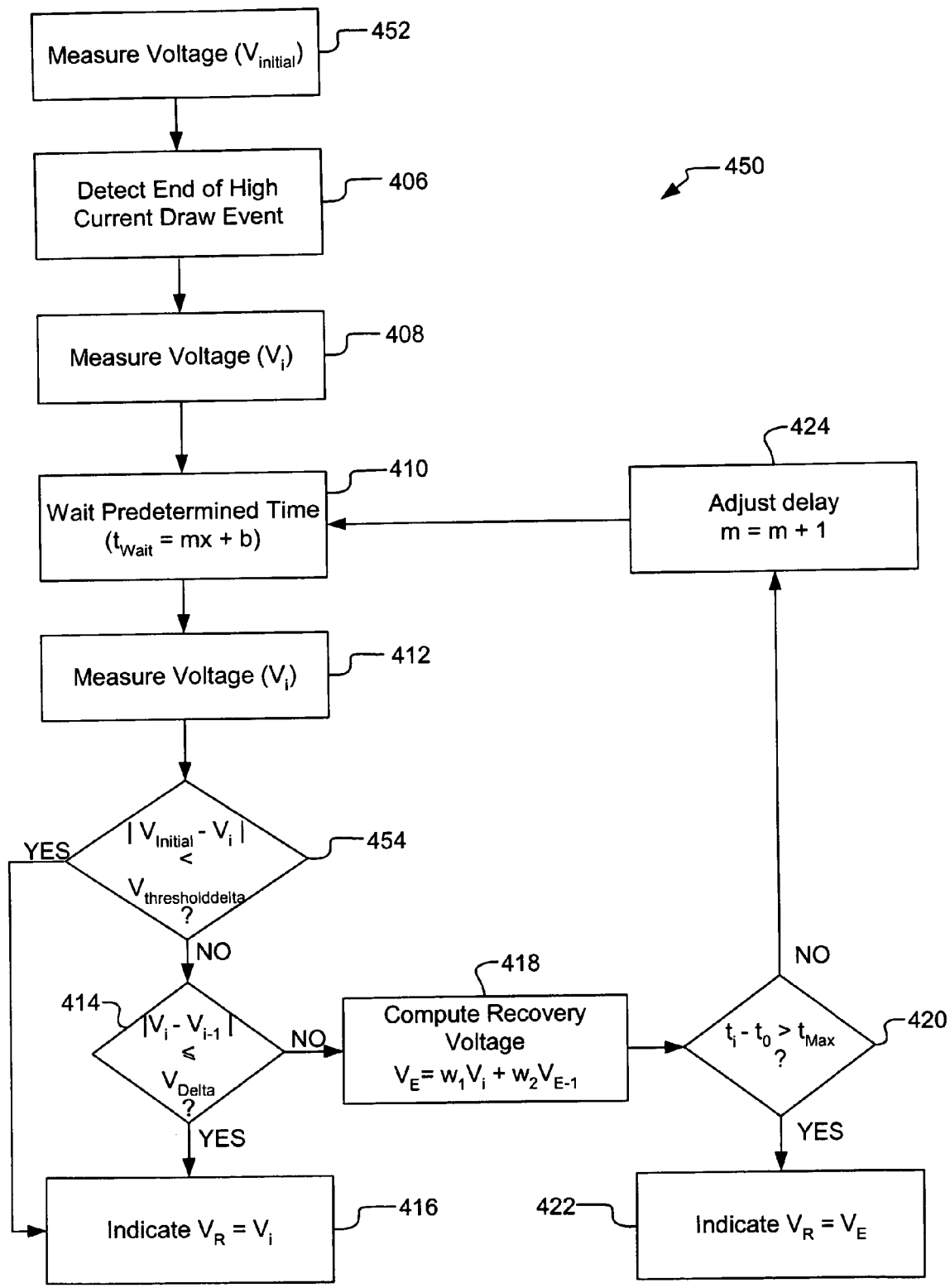

FIGS. 4A and 4B illustrate another algorithm 400 having exemplary operations for determining a valid recovery voltage that can be used to determine battery status. The algorithm 400 may be carried out by the device 200 shown in FIG. 2. Alternatively, the algorithm may be carried out by a device other than that shown in FIG. 2. FIG. 4A is a graph 402 showing voltage response 404 to a transient increased current draw event that starts at time $t_{start}$ and ends at time $t_{end}$.

Generally, the recovery voltage determination algorithm 400 depicted by FIGS. 4A and 4B analyzes rate of change in voltage over time during the recovery period. FIG. 4A shows two exemplary voltages, $V_i$ and $V_{i-1}$, measured at times $t_i$ and $t_{i-1}$, respectively (for i≧1). As is discussed with respect to FIG. 4B, a number of voltages $V_i$ and $V_{i-1}$ associated with different values of 'i' are used to determine the change in voltage over time. When the change in the voltages ($V_i - V_{i-1}$) reaches a specified minimum threshold ($V_{Delta}$), then the voltage $V_i$ is considered a valid recovery voltage. If the change does not reach the specified minimum after a maximum time duration, an estimated recovery voltage (described below) is used as the valid recovery voltage.

Referring to FIG. 4B, the algorithm 400 begins with a detecting operation 406 detects the current draw event. The current draw event can be detected in a number of ways, such as those discussed above with respect to FIGS. 2-3. The detecting operation 406 detects at least the end of the transient increased current draw event, and may also detect the start of the transient increased current draw event. After the transient increased current draw event ends, the recovery period begins. It is during the recovery period that the algorithm 400 evaluates battery voltage to determine recovery voltage.

At some time, $t_i$, after the transient increased current draw event ends, a measuring operation 408 measures voltage $V_i$. $V_i$ will serve as a basis for the first calculation of the change in voltage. Prior to obtaining another voltage measurement, a waiting operation 412 waits a time duration, $t_{wait}$. Time duration $t_{wait}$ represents a time interval between adjacent voltage measurements. In the embodiment shown, $t_{wait}$ is a function of a value 'x'. The value 'x' is a fixed value representing a minimum time increment. According to the embodiment in FIG. 4B, the time interval $t_{wait}$ is calculated with the following equation:

$$t_{wait} = mx + b. \quad \text{Eq. (3)}$$

Equation (3) is readily recognizable as the equation for a straight line. In a particular embodiment the values of 'm', 'x', and 'b' are initially set to 1, 10 msec, and 0, respectively; however, 'm', 'x', and 'b' are not limited to these values. In other embodiments, a different function may be used to calculate $t_{wait}$.

After waiting time duration $t_{wait}$, another measuring operation 412 measures the battery voltage again. The voltage measured in the measuring operation 412 is referred to as $V_i$, because the current time is designated as $t_i$. The voltage measured in the previous measuring operation 410 is now designated as $V_{i-1}$.

A determining operation 414 determines whether the change in voltage measured at times $t_i$ and $t_{i-1}$ is greater than a specified voltage change, $V_{Delta}$. In one embodiment, $V_{Delta}$ is equal to 0.010 volts. In the embodiment shown, the voltage change is calculated using the absolute value of the difference in voltages $V_i$ and $V_{i-1}$. In this embodiment, the absolute value is used to take into account voltage overshoot during the recovery period. In other embodiments where voltage overshoot is not likely, the absolute value need not be used.

In the embodiment shown, if the value given by $|V_i - V_{i-1}|$ is less than or equal to $V_{Delta}$, then the algorithm 400 branches "YES" to an indicating operation 416. The indicating operation 416 indicates that the valid value for the battery voltage is $V_i$. One embodiment of the indicating operation 416 stores the value $V_i$ for later retrieval. In another embodiment, the indicating operation 416 uploads the value $V_i$ to another device, using telemetry or another communication mechanism. In yet another embodiment, the indicating operation 416 outputs the value $V_i$ on a display.

Referring again to the determining operation 414, if the change in voltage is greater than $V_{Delta}$, the algorithm branches "NO" to a computing operation 418. The computing operation 418 computes an estimated recovery voltage, $V_E$. The estimated recovery voltage, $V_E$, generally represents an estimate of the final voltage to which the battery voltage will eventually recover. One embodiment of the computing operation 418 computes $V_E$ according to a function as given in Equation (4) below:

$$V_E = w_1 * V_1 + w_2 * V_{E-1}, \quad \text{Eq. (4)}$$

wherein $w_1$ and $w_2$ are weights assigned to $V_i$ and $V_{E-1}$, respectively. Equation 2 will be recognized as a moving average of voltage $V_i$. In one embodiment, $w_1$ is set equal to ⅛ and $w_2$ is set equal to ⅞; however, $w_1$ and $w_2$ are not limited to these values. In other embodiments, a different function may be used to estimate $V_R$.

Another determining operation 420 determines whether a threshold amount of time has passed since the end of the transient increased current draw event. In this embodiment, it is determined whether $(t_i - t_{end})$ is greater than $t_{Max}$, wherein $t_{Max}$ is the specified threshold time duration. The threshold value $t_{Max}$ is set to a value that is appropriate to the particular application, such as 48 hours or more.

If the determining operation 420 determines that the elapsed time is greater than the threshold time duration, $t_{Max}$, the algorithm 400 branches "YES" to an indicating operation 422. The indicating operation 422 selects the recovery voltage, $V_E$, as the recovery voltage, $V_R$, and indicates the status of the voltage as valid. As a result, the estimated recovery voltage $V_E$ is used as the recovery voltage when the algorithm 400 fails to converge on a valid voltage within the threshold time, $t_{Max}$. Defaulting to $V_E$ in this manner may be particularly appropriate in PG devices, in which consecutive voltage differences may not converge to within $V_{Delta}$. For example, repeated high voltage shocks or repeated telemetry transmission could restart the transient effects of a transient increased current event, such that voltage change never is within $V_{Delta}$. Also, late-life depletion can cause a natural voltage decline, such that a transient increased current event might put the battery voltage on a more steep slope from which the battery never recovers. Therefore, the determining operation 420 ensures that a valid recovery voltage is eventually indicated to determine battery health.

If, in the determining operation 420, it is determined that the elapsed time is not greater than the threshold time duration, $t_{Max}$, the algorithm branches "NO" to an adjusting operation 424. The adjusting operation 424 adjusts one or more of the parameters used to calculate $t_{wait}$ in the waiting operation 410. As shown in the particular embodiment, the adjusting operation 424 increments 'm' by one; however, the adjustment to 'm' is not limited to incrementing by one. In one particular embodiment, 'm' is capped at 360000. In other embodiments, other parameters may be adjusted to vary $t_{Wait}$.

In the embodiment shown, the effect of the adjusting operation 424 is to cause $t_{Wait}$ to be longer in subsequent iterations through the algorithm 400. In many applications it is desirable to increase $t_{Wait}$ during the recovery period because typically battery voltage recovers in an asymptotic fashion. By delaying longer to take subsequent measurements of voltage, useless measurements are avoided, thereby using less energy and/or processor time. Although the illustrated embodiment results in an increase of $t_{Wait}$ for subsequent voltage measurements, it is to be understood that variation of $t_{wait}$ is not limited to increases. In other embodiments, $t_{Wait}$ may vary in any manner between adjacent measurements, including decreasing, increasing, and/or staying constant.

After the adjusting operation 424, the algorithm 400 returns to the waiting operation 410. The waiting operation 410 again waits a time duration given by $t_{Wait}$, but $t_{Wait}$ may be different from the previous iteration of the waiting operation 410, by virtue of the adjusting operation 424. After waiting the time duration $t_{Wait}$, the measuring operation 412 again measures battery voltage, $V_i$. It should be noted that previous measurement of voltage in measuring operation 412 is now designated $V_{i-1}$. The algorithm 400 continues looping in this fashion until the measured voltage change is no longer greater than $V_{Delta}$, or $t_{Max}$ time has passed.

Those skilled in the art will recognize that waiting operation 410, measuring 412, and determining operation 414 together evaluate the first derivative of voltage with respect to time. Other embodiments may evaluate the second derivative of voltage. Still other embodiments may evaluate other functions of voltage measurements. In addition, embodiments are not restricted to using adjacent voltage measurements. Because of inherent random noise in voltage measurement circuitry, one embodiment can use multiple voltage derivative (dv/dt) measurements at multiple times to increase accuracy.

FIG. 4C depicts another embodiment of a voltage recovery determination algorithm 450. The embodiment shown in FIG. 4C is similar to the embodiment shown in FIG. 4B, but includes additional operations. Specifically, an initial measuring operation 452 measures an initial steady-state voltage, $V_{Initial}$, prior to detecting the transient increased current draw event. $V_{Initial}$ is used later in another determining operation 454, which determines whether the most recently measured voltage, $V_i$, has recovered to within a specified range of $V_{Initial}$. Specifically, the embodiment of the determining operation 454 computes Equation (5):

$$|V_{initial} - V_i| < V_{thresholddelta}, \quad \text{Eq. (5):}$$

wherein $V_{thesholddelta}$ is a specified voltage difference. If the magnitude of difference between $V_{Initial}$ and $V_i$ is less than or equal to $V_{thresholddelta}$, then the recovery voltage determination algorithm 450 branches 'YES' to the indicating operation 420, where $V_R$ is set equal to $V_i$. Otherwise, the algorithm 450 branches 'NO' to the determining operation 418, which is described above.

Figure 5A:
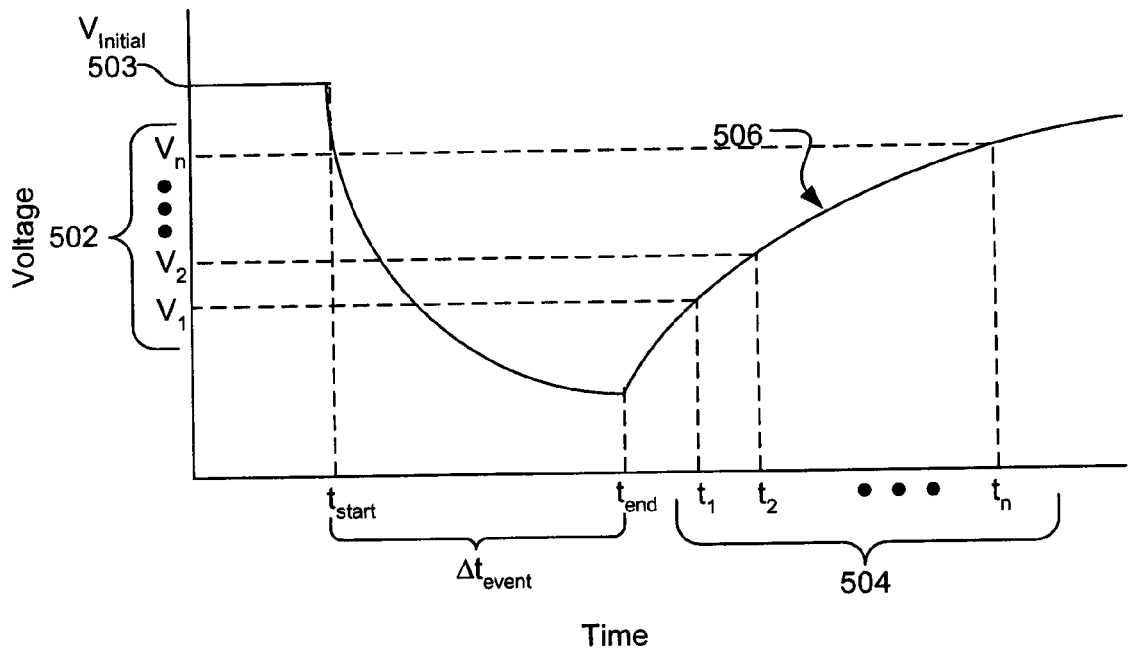
FIGS. 5A-5B illustrate yet another exemplary algorithm for determining recovery voltage using a prediction based on voltage measured during recovery.
Figure 5B:
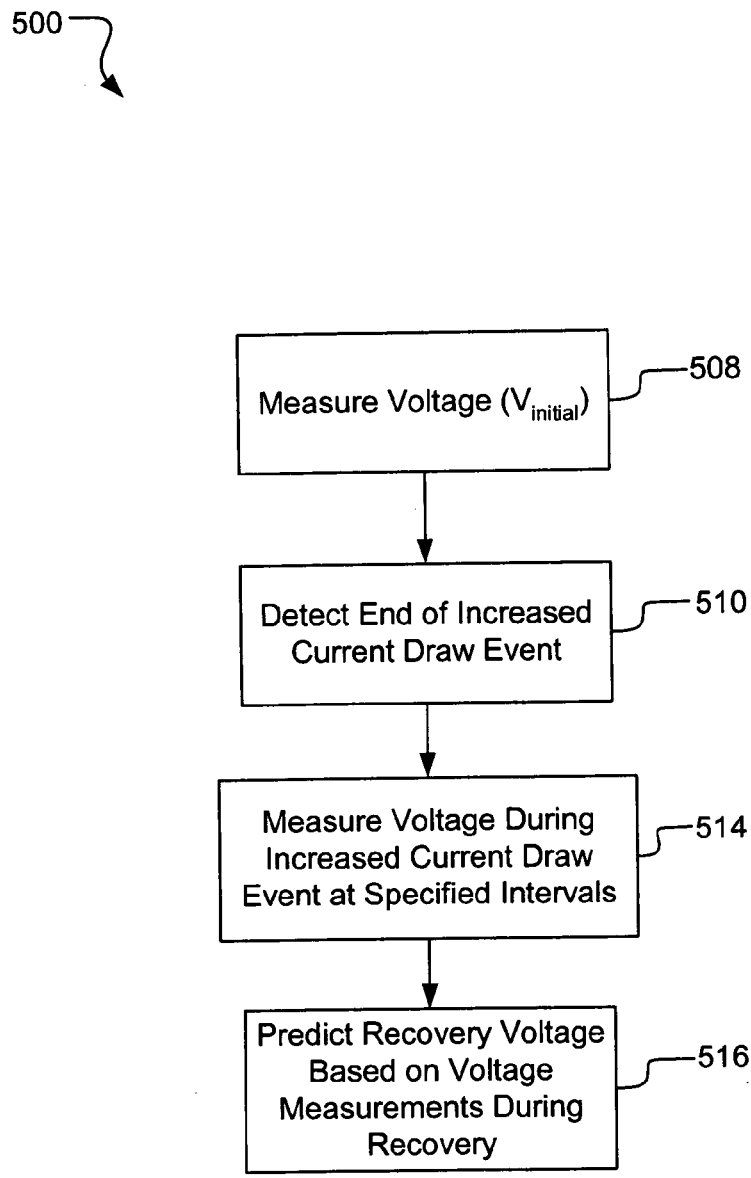

FIGS. 5A-5B illustrate yet another exemplary algorithm 500 for determining recovery voltage using a prediction based on conditions related to the transient increased current event and other battery conditions. In this embodiment, one or more voltages $V_1 - V_n$ 502 measured at times, $t_1 - t_n$ 504, during recovery period 506. The voltages $V_1 - V_n$ 502 can then be used to predict the recovery voltage. Optionally, other battery conditions can be used to predict the recovery voltage.

The embodiment of the recovery voltage determination algorithm 500 begins with an optional measuring operation 508 that measures an initial voltage 503 prior to detection of a transient increased current draw event. A detecting operation 510 then detects the transient increased current draw event. The detecting operation 510 detects at least the end of the transient increased current draw event, but could also detect the start of the transient increased current draw event. The transient increased current draw event can be detected in a number of ways, such as those discussed above with respect to FIGS. 2-3.

Another measuring operation 514 measures battery voltages 502 at corresponding specified times $t_1 - t_n$ 504 following the end of the transient increased current draw event. One embodiment of the measuring operation 514 includes a looping function that measures battery voltage at specific times during recovery. In some embodiments, the difference in time between successive voltage measurements can depend on various battery conditions such as the battery chemistry. In a particular embodiment, the time interval between measurements is longer than two seconds. The time interval need not be periodic, but can vary (e.g., linearly, and logarithmically are two likely candidates). The looping function will end after a specified time or after the voltage reaches a specified level or following a specified number of measurements. The measured voltages are saved in memory.

A predicting operation 516 reads the voltages 502 and predicts a recovery voltage based on the measured voltages 502. One embodiment of the predicting operation fits the voltages 502 to a curve using curve fitting equations to determine the recovery voltage. This embodiment is expressed in Equation (6):

$$V_R = f_2(V_1, V_2, \ldots, V_n), \quad \text{Eq. (6):}$$

wherein $V_R$ represents the predicted recovery voltage. In another embodiment, the recovery voltage is determined using a lookup table that has known voltage recovery profile data stored therein. This embodiment is expressed in Equation (7):

$$V_R = \text{Lookup}(V_1, V_2, \ldots, V_n) \quad \text{Eq. (7):}$$

The operations involved in the predicting operation 516 can be carried out by the battery-powered device, or alternatively by a computing device that is in communication with the battery-powered device.

In other embodiments of the predicting operation 516, battery conditions are used in addition to the voltage measurements to determine $V_R$. In these embodiments, the initial voltage measurement 503 (obtained in the measuring operation 508) is used to determine a degree of voltage change due to the transient increased current draw event. Equation (8) below expresses a function of the initial voltage measurement, $V_{Initial}$:

$$V_R = f(V_{Initial}, V_1, V_2, \ldots, V_n). \quad \text{Eq. (8):}$$

In another embodiment, the duration of the transient increased current draw event is used as a determinant in the function, as shown in Eq. (9):

$$V_R = f(V_{initial}, \Delta t_{event}, V_1, V_2, \ldots, V_n). \quad \text{Eq. (9):}$$

In yet another embodiment, charge consumption $Q_{start}$ is used as a determinant in the function, as shown in Eq. (10):

$$V_R = f(V_{Initial}, \Delta t_{event}, Q, V_1, V_2, \ldots, V_n). \quad \text{Eq. (10):}$$

Charge consumption can be estimated, or measured (e.g., based on measurement circuitry such as a coulometer or current measurement during the event).

Although some exemplary methods, systems, and devices have been illustrated in the accompanying drawing and described in the foregoing detailed description, it will be understood that the methods and systems shown and described are not limited to the particular embodiments described herein, but rather are capable of numerous rearrangements, modifications, and substitutions without departing from the scope and spirit of the claims set forth below.

What is claimed is:

1. A method for determining a recovery voltage associated with a battery, the method comprising:
    detecting a transient increased current draw event that draws current from the battery at a current level that is greater than a steady-state average current level, the transient increased current draw event starting at a start time and ending at an end time;
    selecting a battery voltage measurement obtained after the end time based on time-related or voltage-related criteria; and
    determining the recovery voltage using the battery voltage measurement, wherein the recovery voltage represents a voltage level to which battery voltage is expected to recover after the transient increased current draw event.

2. A method as recited in claim 1 wherein selecting comprises:
    determining a time duration to wait prior to obtaining the battery voltage measurement, wherein the time duration is determined based on one or more battery conditions including battery chemistry, type of transient increased current draw event, duration of the transient increased current draw event, magnitude of voltage change during the transient increased current draw event, and temperature; and
    measuring battery voltage after the time duration has passed.

3. A method as recited in claim 2 further comprising:
    obtaining multiple battery voltage measurements at predetermined time intervals after the time duration has passed; and
    wherein determining the recovery voltage comprises fitting multiple voltage measurements to a curve.

4. A method as recited in claim 1 wherein selecting a measured battery voltage comprises obtaining multiple battery voltage measurements at associated times after the end time, wherein intervals between adjacent times are determined according to a function.

5. A method as recited in claim 1, further comprising taking a derivative of voltage with respect to time.

6. A method as recited in claim 5 further comprising taking a multiple order derivative with respect to time.

7. A method as recited in claim 1 further comprising:
    obtaining an initial voltage measurement prior to the transient increased current draw event; and
    wherein the voltage-criteria specifies a minimum threshold voltage difference; and
    wherein determining the recovery voltage comprises setting the recovery voltage equal to the battery voltage measurement if the difference between the initial voltage measurement and the battery voltage measurement is less than or equal to the minimum threshold voltage difference.

8. A computer-readable medium having processor-executable instructions, which when executed by a processor cause the processor to perform a process for determining a recovery voltage associated with a battery, the process comprising:
    detecting a transient increased current draw event that draws current from the battery at a current level that is greater than a steady-state average current level, the transient increased current draw event starting at a start time and ending at an end time;
    obtaining a first measured battery voltage at a first measurement time after the end time;
    obtaining a subsequent measured battery voltage at a subsequent measurement time after the first measurement time; and
    determining the recovery voltage by determining whether the difference between the first measured battery voltage and the subsequent measured battery voltage is less than a specified voltage change.

9. A computer-readable medium as recited in claim 8 wherein the process for determining the recovery voltage further comprises:
    iteratively obtaining one or more other subsequent measured battery voltages at corresponding subsequent measurement times after the end time, wherein time durations between adjacent subsequent measurement times are variable; and
    comparing successive differences between subsequent measured battery voltages to determine if a change in battery voltage is less than the specified voltage change.

10. A computer-readable medium as recited in claim 8, wherein the process for determining the recovery voltage further comprises:
    determining an estimated recovery voltage based on a function of the first measured battery voltage and the subsequent measured battery voltage measured; and
    if time between the subsequent measurement time and the end time is greater than a specified maximum time, using the estimated recovery voltage to determine charge remaining in the battery.

11. A computer-readable medium as recited in claim 8, wherein the process for determining the recovery voltage further comprises:
    obtaining an initial battery voltage measurement prior to the start time;
    determining whether a magnitude of difference between the initial battery voltage and a selected one of the first measured battery voltage and the subsequent measured battery voltage is less than a specified threshold value; and
    if the magnitude of difference is less than the specified threshold value, setting the recovery voltage equal to the selected one of the first measured battery voltage and the subsequent measured battery voltage.

12. An implantable pulse generator (PG) device operable to stimulate an organ, the PG device comprising:
    a battery;

a power sink drawing current from the battery at a steady-state level when a high current function is deactivated and drawing current from the battery at an increased level when the high current function is activated, wherein drawing current at the increased level causes a drop in battery voltage and a subsequent return to drawing current at the steady-state level causes an increase in battery voltage toward a recovery voltage;

a control module controlling the power sink and triggering a transient increased current draw event comprising drawing current at the increased level for a time period followed by drawing current at the steady-state level; and a status indicator module detecting the transient increased current draw event and waiting a minimum time duration after the transient increased current draw event to determine the recovery voltage using a battery voltage measurement.

13. A PG device as recited in claim 12, further comprising:

a memory having stored thereon a value representing a time duration, and wherein the status indicator module determines the minimum time by retrieving the value from the memory.

14. A PG device as recited in claim 12 wherein the status indicator module determines the recovery voltage based on a rate of change in battery voltage during a voltage recovery period after the transient increased current draw event.

15. A PG device as recited in claim 14 wherein the status indicator module measures multiple voltages, each of the multiple voltages measured at a time determined according to a function of a minimum time increment, and wherein the time interval between each voltage measurement is variable.

16. A PG device as recited in claim 12 wherein the power sink comprises one or more of a beeper, telemetry circuitry, or a high-voltage charge circuitry.

17. A PG device as recited in claim 12 wherein the status indicator module measures multiple voltages taken at predetermined time intervals during a voltage recovery period and predicts the recovery voltage based on the multiple voltage measurements.

18. A PG device as recited in claim 17 wherein the status indicator module predicts the recovery voltage by fitting the multiple voltage measurements to a curve.

19. A PG device as recited in claim 17 wherein the status indicator module predicts the recovery voltage based on one or more of the multiple voltage measurements, the battery voltage prior to the transient increased current draw event, the duration of the event, the magnitude of charge used during the event.

20. A system comprising:

a power sink requiring power to operate;

a battery delivering increased current to the power sink at a specified time, wherein delivery of increased current to the power sink causes a drop in battery voltage and a subsequent voltage recovery; and means for determining a recovery voltage using a battery voltage measurement, wherein determining the recover voltage includes computing a rate of change of voltage during the voltage recovery.

21. A system as recited in claim 20, wherein the means for determining comprises:

a memory having stored thereon microprocessor-executable instructions; and a microprocessor retrieving the instructions from the memory.

22. A system as recited in claim 20, wherein the means for determining implements a method comprising:

determining an absolute value of the difference between a first voltage measurement and a second voltage measurement;

if the absolute value of the difference is less than a specified voltage difference, using the second voltage measurement to determine remaining charge in the battery;

if the absolute value of the difference is not less than the specified voltage difference, computing an estimated recovery voltage based on at least a function of the first and second voltage measurements; and if the elapsed time since the specified time is greater than a maximum time, using the estimated recovery voltage to determine remaining charge in the battery.

23. A system as recited in claim 20 wherein the means for determining a recovery voltage comprises determining a minimum time to wait after delivering increased current before measuring battery voltage, and wherein the minimum time to wait is based on at least one of the magnitude of the drop in battery voltage, the type of battery, the length of time of delivery of current to the power sink, and the type of power sink.

* * * * *